United States Patent
Teixeira et al.

(10) Patent No.: US 9,173,574 B2
(45) Date of Patent: Nov. 3, 2015

(54) MECHANICAL HEALTH MONITOR APPARATUS AND METHOD OF OPERATION THEREFOR

(76) Inventors: Rodrigo E. Teixeira, Madison, AL (US); Alton Reich, Huntsville, AL (US)

( * ) Notice: Subject to any disclaimer, the term of this patent is extended or adjusted under 35 U.S.C. 154(b) by 504 days.

(21) Appl. No.: 13/096,845

(22) Filed: Apr. 28, 2011

(65) Prior Publication Data

US 2012/0022805 A1 Jan. 26, 2012

Related U.S. Application Data (63) Continuation-in-part of application No. 12/796,512, filed on Jun. 8, 2010, now Pat. No. 9,060,722, which is a continuation-in-part of application No. 12/640,278, filed on Dec. 17, 2009.

(60) Provisional application No. 61/171,802, filed on Apr. 22, 2009, provisional application No. 61/366,427, filed on Jul. 21, 2010, provisional application No. 61/372,190, filed on Aug. 10, 2010, provisional application No. 61/373,809, filed on Aug. 14, 2010.

(51) Int. Cl.
| | |
|---|---|
| *G01F 23/00* | (2006.01) |
| *A61B 5/0205* | (2006.01) |
| *A61B 5/1455* | (2006.01) |
| *A61B 5/00* | (2006.01) |
| *A61B 5/0402* | (2006.01) |

(52) U.S. Cl.
CPC ............ *A61B 5/0205* (2013.01); *A61B 5/14551* (2013.01); *A61B 5/7203* (2013.01); *A61B 5/7214* (2013.01); *A61B 5/7278* (2013.01); *A61B 5/0402* (2013.01)

(58) Field of Classification Search
USPC ......................................................... 702/50
See application file for complete search history.

(56) References Cited

U.S. PATENT DOCUMENTS

| | | | |
|---|---|---|---|
| 4,802,486 | A | 2/1989 | Goodman et al. |
| 5,626,140 | A | 5/1997 | Feldman et al. |

(Continued)

FOREIGN PATENT DOCUMENTS

WO  WO 2008/055173 A2  5/2008

OTHER PUBLICATIONS

Matthew Watson, Dynamic Modeling and Wear-Based Remaining Useful Life Prediction of High Power Clutch Systems, December 2005, Tribology & Lubrication Technology, pp. 72-82.*

(Continued)

*Primary Examiner* — Tung S Lau
(74) *Attorney, Agent, or Firm* — Kevin Hazen (57) ABSTRACT

A probabilistic data signal processor used to determine health of a system is described. Initial probability distribution functions are input to a dynamic state-space model, which iteratively operates on probability distribution functions, such as state and model probability distribution functions, to generate a prior probability distribution function, which is input to a probabilistic updater. The probabilistic updater integrates sensor data with the prior to generate a posterior probability distribution function passed to a probabilistic sampler, which estimates one or more parameters using the posterior, which is output or re-sampled and used as an input to the dynamic state-space model in the iterative algorithm. In various embodiments, the probabilistic data signal processor is used to filter output from any mechanical device using appropriate physical models, which optionally include chemical, electrical, optical, mechanical, or fluid based models. Examples to valve bearings and pipe systems are provided.

16 Claims, 9 Drawing Sheets

(56) References Cited

U.S. PATENT DOCUMENTS

| | | | |
|---|---|---|---|
| 5,853,364 | A | 12/1998 | Baker |
| 6,405,108 | B1 | 6/2002 | Patel |
| 6,463,311 | B1 | 10/2002 | Diab |
| 6,505,145 | B1 | 1/2003 | Bjornson |
| 6,511,436 | B1 | 1/2003 | Asmar |
| 6,728,660 | B2 | 4/2004 | Bjornson |
| 6,882,959 | B2 | 4/2005 | Rui |
| 7,006,947 | B2 | 2/2006 | Tryon |
| 7,016,825 | B1 | 3/2006 | Tryon |
| 7,018,338 | B2 | 3/2006 | Vetter et al. |
| 7,020,507 | B2 | 3/2006 | Scharf |
| 7,027,953 | B2 | 4/2006 | Klein |
| 7,058,550 | B2 | 6/2006 | Kouritzin |
| 7,079,888 | B2 | 7/2006 | Oung et al. |
| 7,149,320 | B2 | 12/2006 | Haykin |
| 7,191,110 | B1 | 3/2007 | Charbel |
| 7,260,501 | B2 | 8/2007 | Pattipatti |
| 7,289,906 | B2 | 10/2007 | Merwe |
| 7,317,770 | B2 | 1/2008 | Wang |
| 7,460,915 | B2 | 12/2008 | Marik et al. |
| 7,480,601 | B2 | 1/2009 | Tryon |
| 7,536,277 | B2 | 5/2009 | Pattipatti |
| 8,494,829 | B2* | 7/2013 | Teixeira ............... 703/11 |
| 2004/0122703 | A1 | 6/2004 | Walker et al. |
| 2004/0171950 | A1 | 9/2004 | Starr et al. |
| 2005/0113703 | A1 | 5/2005 | Farringdon et al. |
| 2005/0143634 | A1 | 6/2005 | Baker et al. |
| 2006/0166176 | A1 | 7/2006 | Lakin |
| 2006/0190217 | A1 | 8/2006 | Lee |
| 2007/0100213 | A1 | 5/2007 | Dossas et al. |
| 2008/0027341 | A1 | 1/2008 | Sackner |
| 2008/0082018 | A1 | 4/2008 | Sackner et al. |
| 2009/0024332 | A1 | 1/2009 | Karlov |
| 2009/0069647 | A1 | 3/2009 | McNames |
| 2010/0228102 | A1 | 9/2010 | Addison et al. |
| 2010/0274102 | A1 | 10/2010 | Teixeira |
| 2011/0077484 | A1 | 3/2011 | Van Slyke et al. |
| 2011/0301436 | A1 | 12/2011 | Teixeira |
| 2012/0022336 | A1* | 1/2012 | Teixeira ............... 600/300 |
| 2012/0022350 | A1* | 1/2012 | Teixeira ............... 600/324 |
| 2012/0022384 | A1* | 1/2012 | Teixeira ............... 600/509 |
| 2012/0022805 | A1 | 1/2012 | Teixeira |
| 2012/0022844 | A1 | 1/2012 | Teixeira |
| 2012/0277545 | A1 | 11/2012 | Teixeira |
| 2014/0275886 | A1 | 9/2014 | Teixeira |

OTHER PUBLICATIONS

"Monitoring Metabolic Status: Predicting Decrements in Physiological and Cognitive Performance During Military", Apr. 2004, pp. 1-4, Report Brief, Institute of Medicine of the National Academies.
"Monitoring Metabolic Status: Predicting Decrements in Physiological and Cognitive Performance", 2004, pp. 1-33, Committee on Metabolic Monitoring for Military Field Applications, Standing Committee on Military Nutrition Research.
Arulampalam, Maskell, and Clapp, "A Tutorial on Particle Filters for Online Nonlinear/Non-Gaussian Bayesian Tracking", Feb. 2002, pp. 1-15, vol. 50, No. 2, IEEE Transactions on Signal Processing.
Boers and Driessen, "Particle Filter Track Before Detect Algorithms" Mar. 12, 2003, pp. 1-23, Thales.
Bokareva, Hu, Kanhere, Ristic, Gordon, Bessell, Rutten, and JHA, "Wireless Sensor Networks for Battlefield Surveillance", Oct. 2006, pp. 1-8, Land Warfare Conference.
Briegel and Tresp, "A Nonlinear State Space Model for the Blood Glucose Metabolism of a Diabetic", May 2002, pp. 228-236, Anwendungsaufsatz.
Clifford, "A Novel Framework for Signal Representation and Source Separation; Applications to Filtering and Segmentation of Biosignals", May 17, 2006. pp. 1-15. WSPC/Instruction File, Massachusetts, USA.
Crisan and Doucet, "A Survey of Convergence Results on Particle Filtering Methods for Practitioners", Mar. 2002, pp. 1-11, vol. 50, No. 3, IEEE Transactions on Signal Processing.
Feuerstein, Parker, and Bouotelle, "Practical Methods for Noise Removal: Applications to Spikes, Nonstationary Quasi-Periodic Noise, and Baseline Drift", May 18, 2009, pp. 1-20, American Chemical Society.
Ford, "Non-Linear and Robust Filtering: From the Kalman Filter to the Particle Filter", Apr. 2002, pp. 1-53, DSTO Aeronautical I and Maritime Research Laboratory, Australia.
Goebel, "Pronostics", Apr. 27, 2010, pp. 1-47, NASA Ames Research Center, Moffett Field, CA.
Hall and Llinas, "An Introduction to Multisensor Data Fusion", Jan. 1997, pp. 1-18, vol. 85, No. 1, Proceedings of the IEEE.
Han, Kim, and Kim, "Development of Real-Time Motion Artifact Reduction Algorithm for a Wearable Photoplethysmography", pp. 1-4, Aug. 23, 2007, Proceedings of the $29^{th}$ Annual International Conference of the IEEE EMBS, Lyon, France.
Hoyt, "Sparnet~Spartan Sensor Network to Improve Medical and Situational Awareness of Foot Soldiers During Field Training", Jan. 9, 2007, pp. 1-2, U.S. Army Research Institute of Environmental Medicine. MA.
Hsiao, Plinval-Salgues, and Miller, "Particle Filters and Their Applications", Apr. 11, 2005, pp. 1-99, Cognitive Robotics.
Huang and Wang, "Overview of Emerging Bayesian Approach to Nonlinear System Identification", Apr. 6, 2006, pp. 1-12, International Workshop on Solving Industrial Control and Optimization Problems, Cramado, Brazil.
Johansen, Doucet, and Davy, "Particle Methods for Maximum Likelihood Estimation in Latent Variable Models", Aug. 31, 2007, pp. 1-11, Springer.
Kueck and Freitas, "Where Do Priors and Causal Models Come From? An Experimental Design Perspective", Apr. 7, 2010, pp. 1-13, University of British Columbia, Technical Report.
Lee, "A Particle Algorithm for Sequential Bayesian Parameter Estimation and Model Selection", Feb. 2, 2002. pp. 1-11, vol. 50, No. 2, IEEE Transactions on Signal Processing.
McSharry and Clifford, "Open-Source Software for Generating Electrocardiogram Signals", Jun. 4, 2004, pp. 1-10, Psys.Med.Biol.
Merwe, "Sigma-Point Kalman Filters for Probabilistic Inference in Dynamic State-Space Models", Apr. 2004, pp. 1-397, Oregon Health and Science University. Oregon.
Merwe, Doucet, Freitas, and Wan, "The Unscented Particle Filter", Aug. 16, 2000, pp. 1-46, Cambridge University Engineering Department, Technical Report.
Parker, "A Model-Based Algorithm for Blood Glucose Control in Type I Diabetic Patients", Feb. 1999, pp. 1-10, vol. 46, No. 2, IEEE Transactions on Biomedical Engineering.
Sameni, "A Nonlinear Bayesian Filtering Framework for the Filtering of Noisy ECG Signals", Apr. 21, 2006, pp. 1-62, Laboratoire des Images et des Signaux, France.
Sameni, Shamsollahi, and Jutten, Muti-Channel Electrocardiogram Denoising Using a Bayesian Filtering Framework, 2006. pp. 1-4, Computer in Cardiology.
Storvik, "Particle Filters for State-Space Models With the Presence of Unknown Static Parameters", Feb. 2002, pp. 281-289, vol. 50, No. 2, IEEE Transactions on Signal Processing.
Thrun, "Particle Filters in Robotics or: How the World Became to Be One Big Bayes Network" Aug. 2, 2002, pp. 1-74, UAI.
Verma, Thrun, and Simmons, "Variable Resolution Particle Filter", Aug. 2003, pp. 1-6, In Proceedings of the International Joint Conference on Artificial Intelligence.
Wegman, Leuenberger, Neuenschwander, and Excoffier, "ABCtoolbox: A Versatile toolkit for Approximate Bayesian Computations", Mar. 4, 2010, BMC Bioinformatics.
Welch and Biship, "An Introduction to the Kalman Filter", Jul. 24, 2006, pp. 1-16, Department of Computer Science University of North Carolina, NC.
Welch, "Team18: The Kalman Filter Learning Tool Dynamic and Measurement Models", Feb. 17, 2003, pp. 1-11, University of North Carolina. NC.

(56) References Cited

OTHER PUBLICATIONS

Wu, Rangaraj, Rangayyan, and NG, "Cancellation of Artifacts in ECG Signals Using a Normalized Adaptive Neural Filter", pp. 1-4, Aug. 23, 2007, Proceedings of the 29$^{th}$ Annual International Conference of the IEEE EMBS, Lyon, France.

Arulampalam et al. IEEE Transactions on Signal Processing, Vol. 50, No. 2, 2002, 174-187.

Lauer, M. Cleveland Clinic Journal of Medicine, vol. 76, Suppl. 2, 2009.

Lendek, Zs, et al., "State Estimation Under Uncertainty: A Survey," 2006 (Lendek).

Matthew Watson, Dynamic Modeling and Wear-Based Remaining Useful Life Prediction of High Power Clutch Systems, Dec. 2005, Tribology & Lubrication Technology, pp. 72-82.

Merwe, "Sigma-Point Kalman Filters for Probabilistic Inference in Dynamic State-Space Models", Apr. 2004, pp. 1-379, Oregon Health and Science University, Oregon.

Proceedings of the IEEE, 85, No. 1, 1997, pp. 6-23.

Rutledge, G., "Dynamic Selection of Models," 1995 (Rutledge).

Saatci, E. et al., Dual Unscented Kalman Filter and Its Applications to Respiratory System Modelling,: Source: Kalman Filter: Recent Advances and Applications, Book edited by: Victor M. Moreno and Alberto Pigazo pp. 584, Apr. 2009, I-Tech, Vienna, Austria.

Singer et al. Pub Med PMID:3063772, abstract ( J Electrocardiol. 1988;21 Suppl:S46-S55).

Wukitsch et al., Journal of Clinical Monitoring, vol. 4, pp. 290-301, 1998.

\* cited by examiner

MECHANICAL HEALTH MONITOR APPARATUS AND METHOD OF OPERATION THEREFOR

CROSS-REFERENCES TO RELATED APPLICATIONS

This application claims:
priority to U.S. patent application Ser. No. 12/796,512, filed Jun. 8, 2010, which claims priority to U.S. patent application Ser. No. 12/640,278, filed Dec. 17, 2009, which under 35 U.S.C. 120 claims benefit of U.S. provisional patent application No. 61/171,802, filed Apr. 22, 2009,
benefit of U.S. provisional patent application No. 61/366,437 filed Jul. 21, 2010;
benefit of U.S. provisional patent application No. 61/372,190 filed Aug. 10, 2010; and
benefit of U.S. provisional patent application No. 61/373,809 filed Aug. 14, 2010,
all of which are incorporated herein in their entirety by this reference thereto.

STATEMENT REGARDING FEDERALLY SPONSORED RESEARCH OR DEVELOPMENT

The U.S. Government may have certain rights to this invention pursuant to Contract Number IIP-0839734 awarded by the National Science Foundation.

BACKGROUND OF THE INVENTION

1. Field of the Invention

The present invention relates generally to apparatus and methods for monitoring mechanical health of an apparatus.

2. Discussion of the Related Art

Any mechanical product will eventually fail. Often, a failure of a component or sub-component results in failure of an overall system. Such failures present safety, time, and financial concerns. Failures are attributable to a plurality of damage mechanisms, such as fatigue, corrosion, and buckling. A method or apparatus for predicting failure of a system, component, or sub-component would allow operators to repair, replace, or retire system components prior to actual failure, which reduces negative consequence of component failure.

Patents related to the current invention are summarized herein.

Deterministic Techniques

Typically, computer-based systems use a mapping between observed symptoms of failure and the equipment where the mapping is built using deterministic techniques. The mapping typically takes the form of a look-up table, a symptom-problem matrix, trend analysis, and production rules.

Vibrational Analysis

R. Klein "Method and System for Diagnostics and Prognostics of a Mechanical System", U.S. Pat. No. 7,027,953 B2 (Apr. 11, 2006) describes a vibrational analysis system for diagnosis of health of a mechanical system by reference to vibration signature data from multiple domains, which aggregates several features applicable to a desired fault for trend analysis of the health of the mechanical system.

Intelligent System

S. Patel, et. al. "Process and System for Developing Predictive Diagnostic Algorithms in a Machine", U.S. Pat. No. 6,405,108 B1 (Jun. 11, 2002) describe a process for developing an algorithm for predicting failures in a system, such as a locomotive, comprising conducting a failure mode analysis to identify a subsystem, collecting expert data on the subsystem, and generating a predicting signal for identifying failure modes, where the system uses external variables that affect the predictive accuracy of the system.

C. Bjornson, "Apparatus and Method for Monitoring and Maintaining Plant Equipment", U.S. Pat. No. 6,505,145 B1 (Jan. 11, 2003) describes a computer system that implements a process for gathering, synthesizing, and analyzing data related to a pump and/or a seal, in which data are gathered, the data is synthesized and analyzed, a root cause is determined, and the system suggests a corrective action.

C. Bjornson, "Apparatus and Method for Monitoring and Maintaining Plant Equipment", U.S. Pat. No. 6,728,660 B2 (Apr. 27, 2004) describes a computer system that implements a process for gathering, synthesizing, and analyzing data related to a pump and/or a seal, in which data are gathered, the data is synthesized and analyzed, and a root cause is determined to allow a non-specialist to properly identify and diagnose a failure associated with a mechanical seal and pump.

K. Pattipatti, et. al. "Intelligent Model-Based Diagnostics for System Monitoring, Diagnosis and Maintenance", U.S. Pat. No. 7,536,277 B2 (May 19, 2009) and K. Pattipatti, et. al. "Intelligent Model-Based Diagnostics for System Monitoring, Diagnosis and Maintenance", U.S. Pat. No. 7,260,501 B2 (Aug. 21, 2007) both describe systems and methods for monitoring, diagnosing, and for condition-based maintenance of a mechanical system, where model-based diagnostic methodologies combine or integrate analytical models and graph-based dependency models to enhance diagnostic performance.

Probabilistic Techniques

Typically, deterministic methods are used to predict failures. A limited number of probability methods have been proposed for determination of component failure. Probability based component failure systems related to the present invention are summarized herein.

Inferred Data

R. Tryon, et. al. "Method and Apparatus for Predicting Failure in a System", U.S. Pat. No. 7,006,947 B2 (Feb. 28, 2006) describe a method and apparatus for predicting system failure or reliability using a computer implemented model relying on probabilistic analysis, where the model uses data obtained from references and data inferred from acquired data. More specifically, the method and apparatus uses a pre-selected probabilistic model operating on a specific load to the system while the system is under operation.

Virtual Prototyping

R. Tryon, et. al. "Method and Apparatus for Predicting Failure of a Component", U.S. Pat. No. 7,016,825 B1 (Mar. 21, 2006) describe a method and apparatus for predicting component failure using a probabilistic model of a material's microstructural-based response to fatigue using virtual prototyping, where the virtual prototyping simulates grain size, grain orientation, and micro-applied stress in fatigue of the component.

R. Tryon, et. al. "Method and Apparatus for Predicting Failure of a Component, and for Determining a Grain Orientation Factor for a Material", U.S. Pat. No. 7,480,601 B2 (Jan. 20, 2009) describe a method and apparatus for predicting component failure using a probabilistic model of a material's microstructural-based response to fatigue using a computer simulation of multiple incarnations of real material behavior or virtual prototyping.

Statement of the Problem

A method or apparatus for predicting failure of a system, component, or sub-component is needed to allow operators to repair, replace, or retire system components prior to actual failure, which reduces negative consequence of component failure.

SUMMARY OF THE INVENTION

The invention comprises use of a probabilistic model estimating a parameter of a mechanical apparatus

DESCRIPTION OF THE FIGURES

A more complete understanding of the present invention is derived by referring to the detailed description and claims when considered in connection with the Figures, wherein like reference numbers refer to similar items throughout the Figures.

FIG. 9 illustrates inputs and internal models for a pipe failure dynamic state-space model in a closed, FIG. 9A; semi-open, FIG. 9B; and open, FIG. 9C, state;

DETAILED DESCRIPTION OF THE INVENTION

The invention comprises use of a method, a system, and/or an apparatus using a probabilistic model for monitoring and/or estimating a parameter of a mechanical apparatus.

In one embodiment, an intelligent data extraction algorithm (IDEA) is used in a system, which combines a dynamic state-space model with a probabilistic digital signal processor to estimate a parameter, such as a mechanical parameter. More particularly, a probabilistic data signal processor used to determine health of a system is described. Initial probability distribution functions are input to a dynamic state-space model, which iteratively operates on probability distribution functions, such as state and model probability distribution functions, to generate a prior probability distribution function, which is input into a probabilistic updater. The probabilistic updater integrates sensor data with the prior to generate a posterior probability distribution function passed to a probabilistic sampler, which estimates one or more parameters using the posterior, which is output or re-sampled and used as an input to the dynamic state-space model in the iterative algorithm. In various embodiments, the probabilistic data signal processor is used to filter output from any mechanical device using appropriate physical models, which optionally include chemical, electrical, optical, mechanical, or fluid based models. Examples to valve bearings and pipe systems are provided.

Intelligent Data Extraction System

Figure 1:
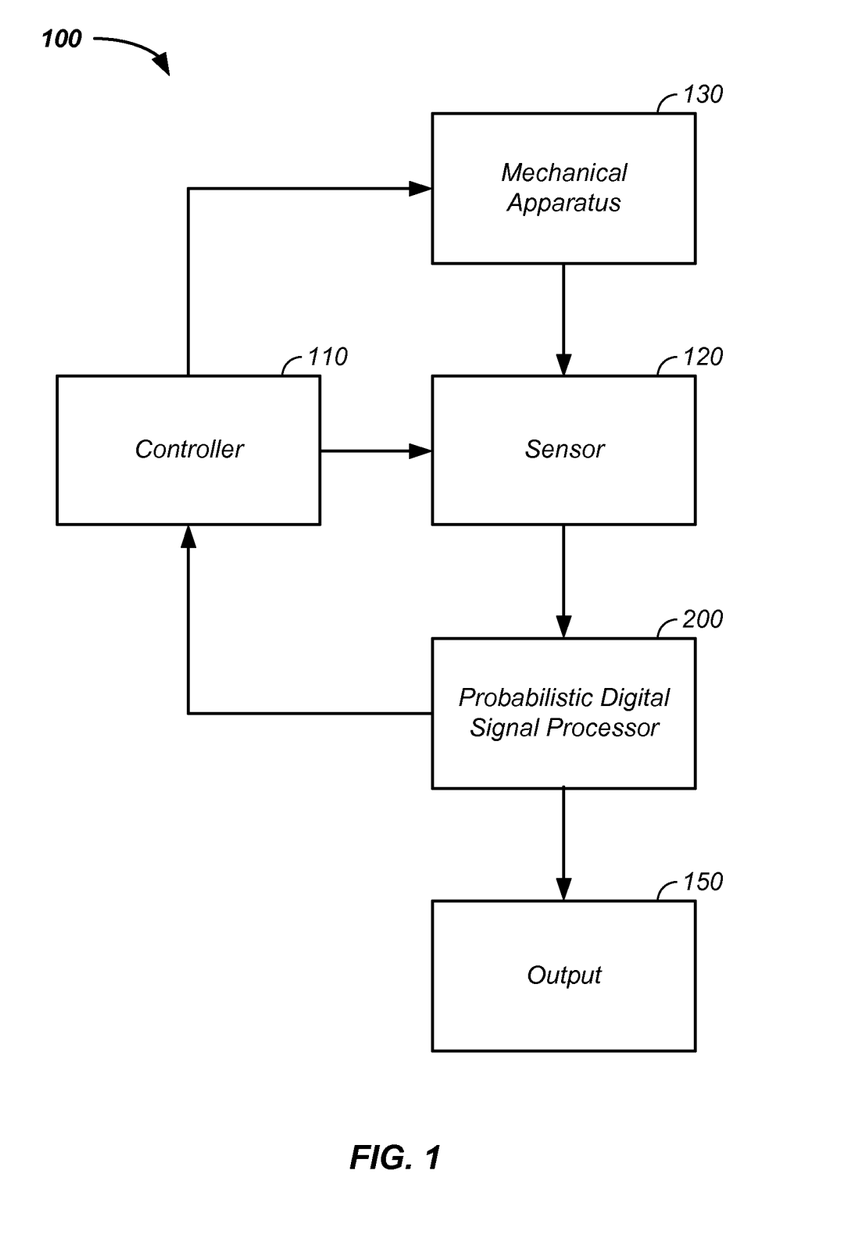
FIG. 1 illustrates operation of an intelligent data extraction algorithm on a mechanical apparatus.

Referring now to FIG. 1, an algorithm based intelligent data extraction system 100 is illustrated. The intelligent data extraction system 100 uses a controller 110 to control a sensor 120 measuring a mechanical apparatus 130. Optionally, the controller 110 additionally controls the mechanical apparatus 130. The sensor 120 provides readings to a data processor or a probabilistic digital signal processor 200, which provides feedback to the controller 110 and/or provides output 150. In one embodiment, the controller 110 comprises a microprocessor in a computer or computer system.

Herein, to enhance understanding and for clarity of presentation, a non-limiting example of an intelligent data extraction system operating on a valve apparatus is used to illustrate methods, systems, and apparatus described herein. Generally, the methods, systems, and apparatus described herein extend to any apparatus having a moveable part. Examples of the dynamic state-space model with a probabilistic digital signal processor used to estimate parameters of additional mechanical systems are provided after the details of the processing engine are presented.

Still referring to FIG. 1, in the valve example the controller 110 controls a sensor 120 measuring opening, closing, or movement of a valve in a mechanical apparatus 130. The sensor 120 provides readings, such as force actuating of the valve, pressure of fluid moving through the valve, and/or angular position of the valve to the probabilistic digital signal processor 200, which is preferably a probability based data processor. The probabilistic digital signal processor 200 provides feedback to the controller 110, such as state of the valve, as part of a loop, iterative loop, time series analysis, and/or generates the output 150, such as the wear, age, or remaining life of the valve. To facilitate the process, the controller 110 optionally moves or rotates the position of the valve and additional sensor readings are collected by the sensor 120 as a function of valve strain and/or temperature. The additional sensor readings are used as input to the probabilistic digital signal processor 200 in the iterative loop. For clarity, the valve apparatus is used repetitively herein as an example of the mechanical apparatus 130 upon which the intelligent data extraction system 100 operates. The probabilistic digital signal processor 200 is further described, infra.

Data Processor

Figure 2:
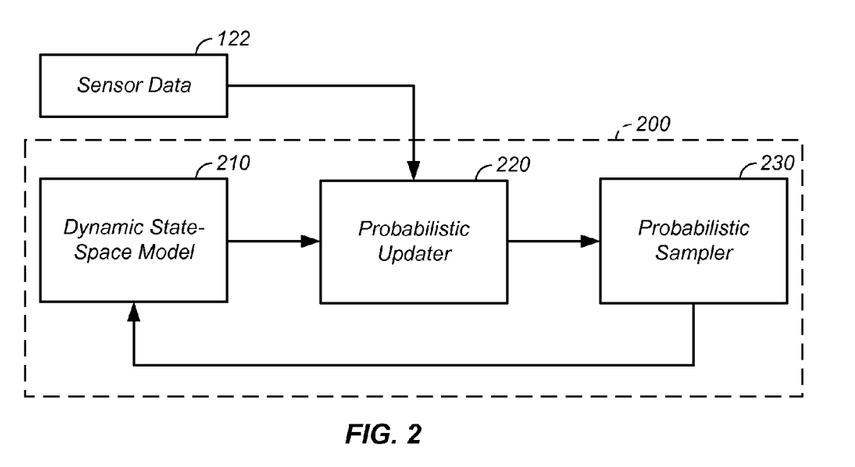
FIG. 2 provides a block diagram of a data processor.

Referring now to FIG. 2, the probabilistic digital signal processor 200 of the intelligent data extraction system 100 is further described. Generally, the data processor includes a dynamic state-space model 210 (DSSM) and a probabilistic updater 220 that iteratively or sequentially operate on sensor data 122 from the sensor 120. The probabilistic updater 220 outputs a probability distribution function to a parameter updater or a probabilistic sampler 230, which generates one or more parameters, such as an estimated diagnostic parameter, which is sent to the controller 110, is used as part of an iterative loop as input to the dynamic state-space model 210, and/or is a basis of the output 150. The dynamic state-space model 210 and probabilistic updater 220 are further described, infra.

Figure 3:
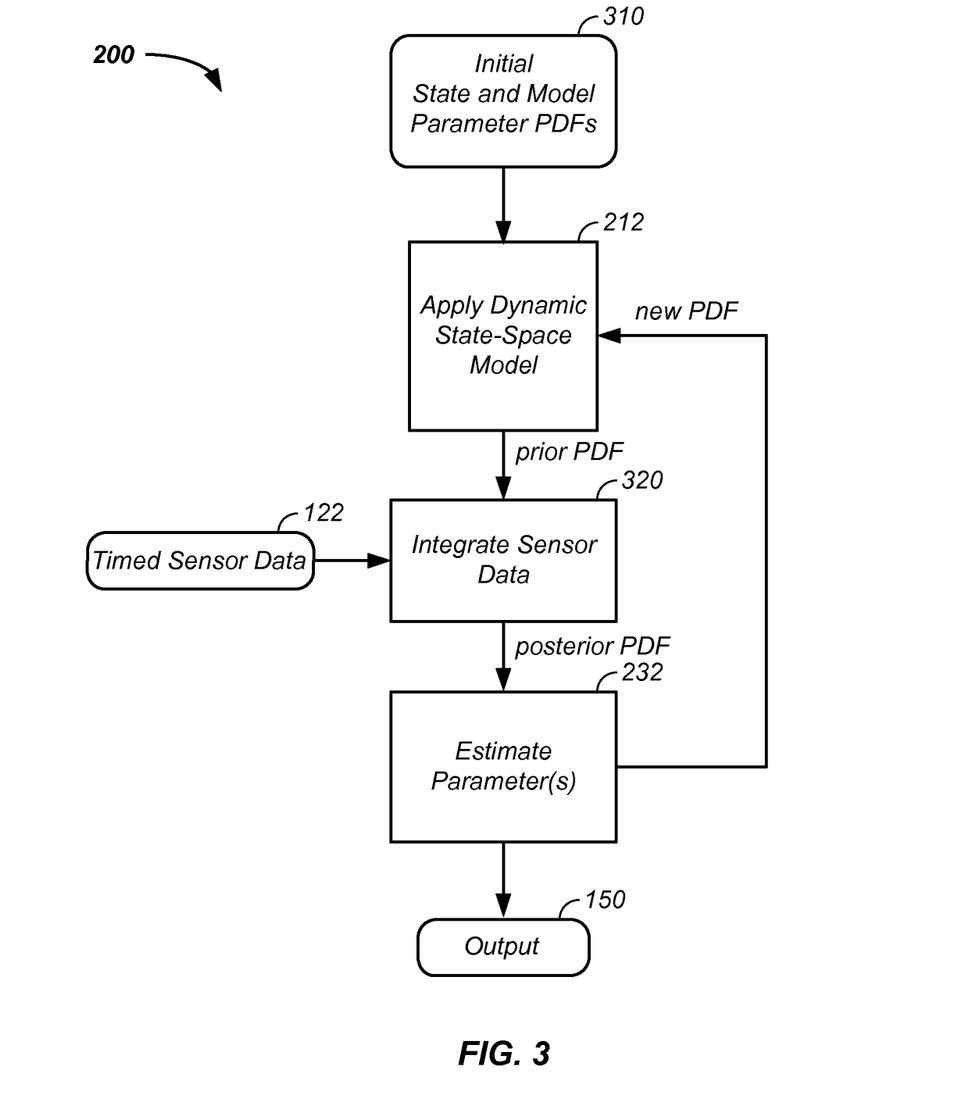
FIG. 3 is a flow diagram of a probabilistic digital signal processor.

Referring now to FIG. 3, the probabilistic digital signal processor 200 is further described. Generally, initial a probability distribution function (PDF) or a set of probability distribution functions 310 (PDFs) are input to the dynamic state-space model 210. In a process 212, the dynamic state-space model 210 operates on the initial probability distribution functions 310 to generate a prior probability distribution function, hereinafter also referred to as a prior or as a prior PDF. For example, an initial state parameter 312 probability distribution function and an initial model parameter 314 probability distribution function are provided as initial inputs to the dynamic state-space model 210. The dynamic state-space model 210 operates on the initial state parameter 312 and/or initial model parameter 314 to generate the prior probability distribution function, which is input to the probabilistic updater 220. In a process 320, the probabilistic updater 220 integrates sensor data, such as timed sensor data 122, by operating on the sensor data and on the prior probabilistic data function to generate a posterior probability distribution function, herein also referred to as a posterior or as a posterior PDF. In a process 232, the probabilistic sampler 230 estimates one or more parameters using the posterior probability distribution function. The probabilistic sampler operates on the state and model parameter probability distribution functions from the state and model parameter updaters 224, 226, respectively or alternatively operates on the joint parameter probability distribution function and calculates an output. The output is optionally:

the state or joint parameter PDF, passed to the PDF resampler 520; and/or output values resulting from an operation on the inputs to the output 150 or output display or the 110 controller In one example, expectation values such as mean and standard deviation of a state parameter are calculated from the state parameter PDF and output to the user, such as for diagnosis. In another example, expectation values, such as the mean value of state and model parameters, are calculated and then used in a model to output a more advanced diagnostic or prognostic parameter. In a third example, expectation values are calculated on a PDF that is the result of an operation on the state parameter PDF and/or model parameter PDF. Optionally, the output is the same as the state parameter PDF or model parameter PDF. Other data, such as user-input data, is optionally used in the output operation. The estimated parameters of the probabilistic sampler 230 are optionally used as a feedback to the dynamic state-space model 210 or are used to estimate a mechanical parameter. The feedback to the dynamic state-space model 210 is also referred to as a new probability function or as a new PDF, which is/are updates of the initial state parameter 312 and/or initial model parameter 314. Again, for clarity, an example of an estimated parameter 232 is wear on the valve.

Dual Estimator

Figure 4:
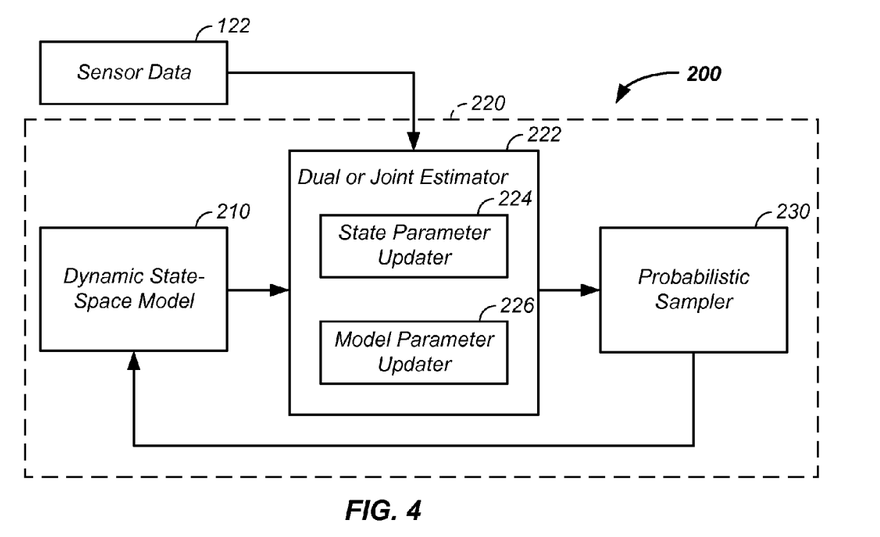
FIG. 4 illustrates a dual estimator.

In another embodiment, the probabilistic updater 220 of the probabilistic digital signal processor 200 uses a dual or joint estimator 222. Referring now to FIG. 4, the joint estimator 222 or dual estimation process uses both a state parameter updater 224 and a model parameter updater 226. Herein, for clarity, a dual estimator 222 is described. However, the techniques and steps described herein for the dual estimator are additionally applicable to a joint estimator as the state parameter and model parameter vector and/or matrix of the dual estimator are merely concatenated in a joint parameter vector and/or matrix in a joint estimator.

State Parameter Updater

A first computational model used in the probabilistic updater 220 includes one or more state variables or state parameters, which correspond to the parameter being estimated by the state parameter updater 224. In the case of the valve apparatus, state parameters include time, the angular position of the valve, and/or an applied pressure on the valve. Some or all state parameters are optionally chosen such that they represent the 'true' value of noisy timed sensor data. In this case, calculation of such posterior state parameter PDF constitutes a noise filtering process and expectation values of the PDF optionally represent filtered sensor values and associated confidence intervals.

Model Parameter Updater

A second computational model used in the probabilistic updater 220 includes one or more model parameters updated in the model parameter updater 226. For example, in the case of the valve apparatus, model parameters include time interval, a bearing friction factor, and/or a variable related to remaining life.

Hence, the dual estimator 222 optionally simultaneously or in an iterative loop updates or calculates both the state parameters and model parameters. The probabilistic sampler 230 is used to determine the estimated value for the mechanical parameter, which is optionally calculated from a state parameter, a model parameter, or a combination of one or more of the state parameter and/or model parameter.

Figure 5:
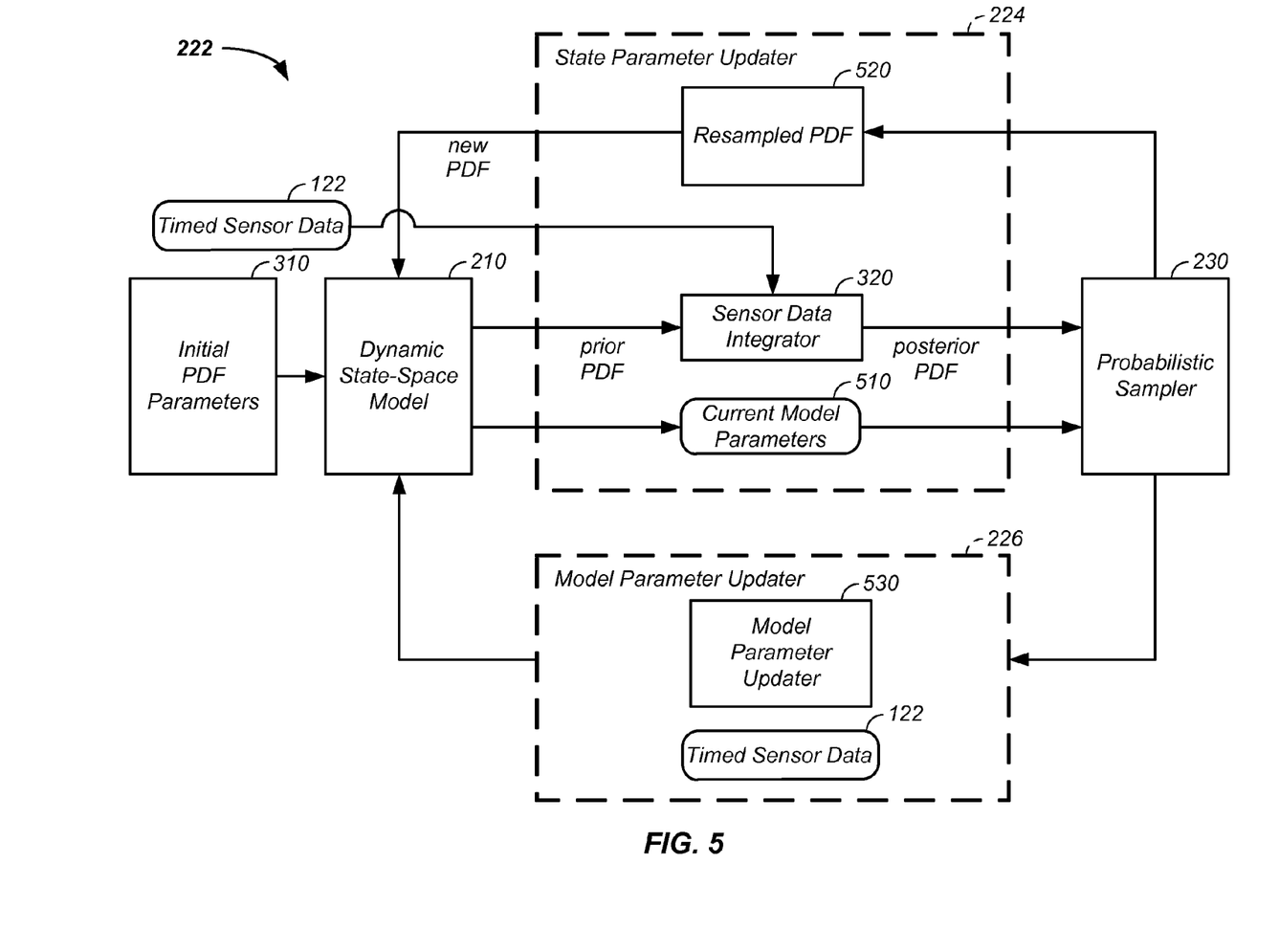
FIG. 5 expands the dual estimator.

Referring still to FIGS. 3 and 4 and now referring to FIG. 5, a first example of the dual estimator 222 is described and placed into context of the dynamic state-space model 210 and probabilistic sampler 230 of the probabilistic digital signal processor 200. The state parameter updater 224 element of the dual estimator 222 optionally:

uses a sensor data integrator 320 operating on the prior PDF being passed from the dynamic state-space model 210, and optionally operates on new timed sensor data 122, to produce the posterior PDF passed to the probabilistic sampler 230;

operates on current model parameters 510; and/or in a process 520, the state parameter updater 224 optionally re-samples a probability distribution function passed from the probabilistic sampler 230 to form the new probability distribution function passed to the dynamic state-space model 210.

In addition, in a process 530 the model parameter updater 226 optionally integrates new timed sensor data 122 with output from the probabilistic sampler 230 to form new input to the dynamic state-space model 210.

Figure 6:
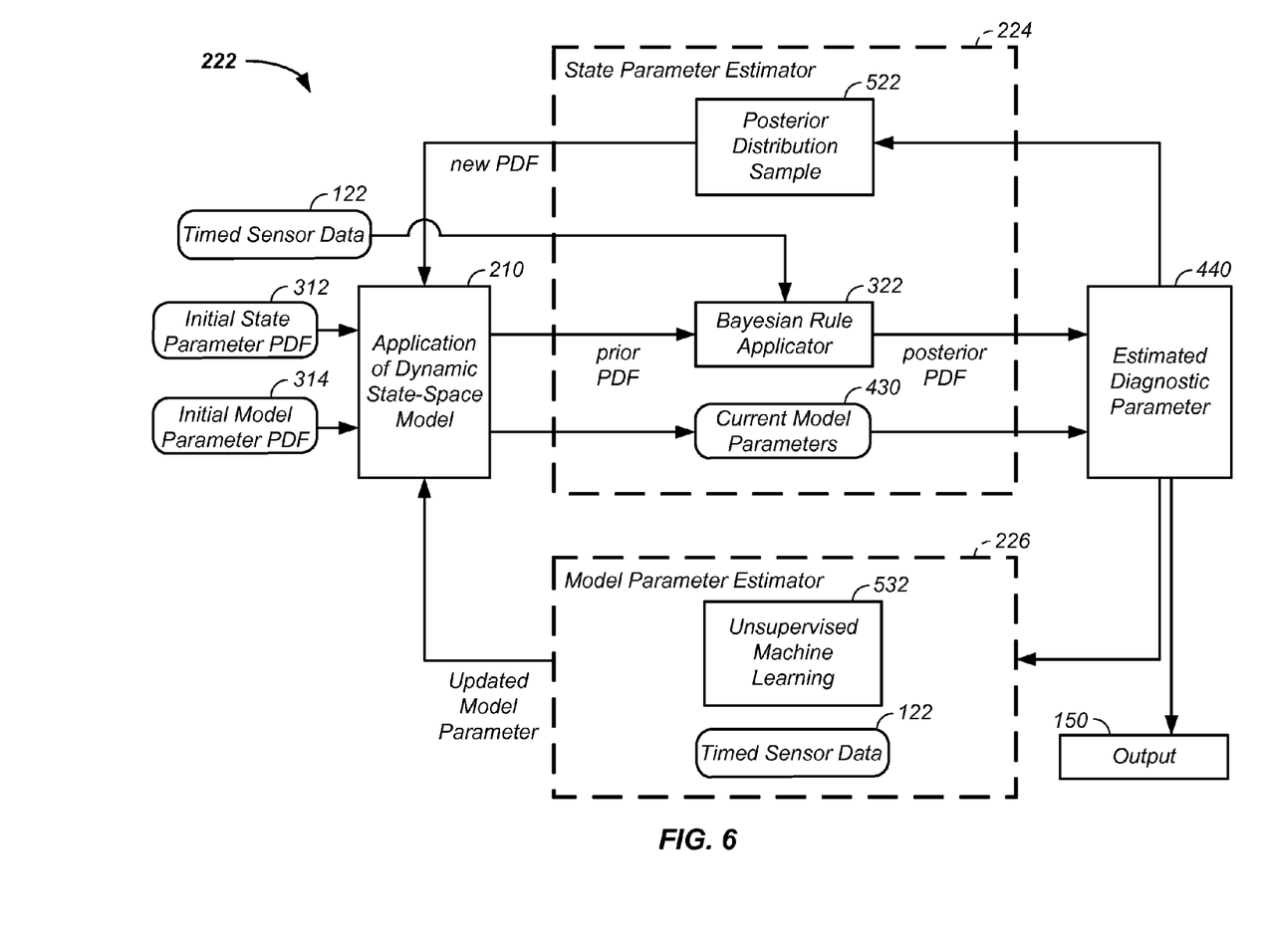
FIG. 6 illustrates state and model parameter estimators.

Referring now to FIG. 6, a second example of a dual estimator 222 is described. In this example:

initial state parameter probability distribution functions 312 are passed to the dynamic state-space model 210; and initial model parameter probability distribution functions 314 are passed to the dynamic state-space model 210;

Further, in this example:

a Bayesian rule applicator 322 is used as an algorithm in the sensor data integrator 320;

a posterior distribution sample algorithm 522 is used as the algorithm in the resampling of the PDF process 520; and an unsupervised machine learning algorithm 532 is used as the algorithm in the model parameter updater 530.

Filtering

In various embodiments, algorithms, data handling steps, and/or numerical recipes are used in a number of the steps and/or processes herein. The inventor has determined that several algorithms are particularly useful: sigma point Kalman filtering, sequential Monte Carlo, and/or use of a sampler. In a first example, either the sigma point Kalman filtering or sequential Monte Carlo algorithms are used in generating the probability distribution function. In a second example, either the sigma point Kalman filtering or sequential Monte Carlo algorithms are used in the unsupervised machine learning 532 step in the model parameter updater 530 to form an updated model parameter. The sigma point Kalman filtering, sequential Monte Carlo algorithms, and use of a sampler are further described, infra.

Sigma Point Kalman Filter

Filtering techniques based on Kalman and extended Kalman techniques offer advantages over conventional methods and work well for filtering linear systems or systems with small nonlinearities and Gaussian noise. These Kalman filters, however, are not optimum for filtering highly nonlinear systems and non-Gaussian/non-stationary noise. In stark contrast, sigma point Kalman filters are well suited to data having nonlinearities and non-Gaussian noise.

Herein, a sigma point Kalman filter (SPKF) refers to a filter using a set of weighted sigma-points that are deterministically calculated, such as by using the mean and square-root decomposition, or an equivalent, of the covariance matrix of a probability distribution function to about capture or completely capture at least the first and second order moments. The sigma-points are subsequently propagated in time through the dynamic state-space model 210 to generate a prior sigma-point set. Then, prior statistics are calculated using tractable functions of the propagated sigma-points and weights, and new measurements.

Sigma point Kalman filters advantages and disadvantages are described herein. A sigma point Kalman filter interprets a noisy measurement in the context of a mathematical model describing the system and measurement dynamics. This gives the sigma point Kalman filter inherent superior performance to all "model-less" methods, such as Wiener filtering, wavelet de-noising, principal component analysis, independent component analysis, nonlinear projective filtering, clustering methods, adaptive noise cancelling, and many others.

A sigma point Kalman filter is superior to the basic Kalman filter, extended Kalman filter, and related variants of the Kalman filters. The extended Kalman filter propagates the random variable using a single measure, usually the mean, and a first order Taylor expansion of the nonlinear dynamic state-space model 210. Conversely, a sigma point Kalman filter decomposes the random variable into distribution moments and propagates those using the unmodified nonlinear dynamic state-space model 210. As a result, the sigma point Kalman filter yields higher accuracy with equal algorithm complexity, while also being easier to implement in practice.

In the sigma-point formalism the probability distribution function is represented by a set of values called sigma points, those values represent the mean and other moments of the distribution which when input into a given function recovers the probability distribution function.

Sequential Monte Carlo

Sequential Monte Carlo (SMC) methods approximate the prior through use of a set of weighted sample values without making assumptions about its form. The samples are then propagated in time through the unmodified dynamic state-space model 210. The resulting samples are used to update the posterior via Bayes rule and the latest noisy measurement or timed sensor data 122.

In the sequential Monte Carlo formalism the PDF is actually discretized into a collection of probability "particles" each representing a segment of the probability density in the PDF.

SPKF and SMC

In general, sequential Monte Carlo methods have analysis advantages compared to the sigma point Kalman filters, but are more computationally expensive. However, the SPKF uses a sigma-point set, which is an exact representation only for Gaussian probability distribution functions (PDFs). As a result, SPKFs lose accuracy when PDFs depart heavily from the Gaussian form, such as with bimodal, heavily-tailed, or nonstationary distributions. Hence, both the SMC and SPKF filters have advantages. However, either a SMC or SPKF is used to propagate the prior using the unmodified DSSM. Generally, when a SMC filter is used a SPKF filter is optionally used and vise-versa.

SPKF or SMC is used to generate a reference signal in the form of a first probability distribution from the model's current (time=t) physiological state. The reference signal probability distribution and a probability distribution generated from a measured signal from a sensor at a subsequent time (time=t+n) are convoluted using Bayesian statistics to estimate the true value of the measured physiological parameter at time=t+n. The probability distribution function is optionally discrete or continuous, and is optionally used to identify the probability of each value of an unidentified random variable (discrete), or the probability of the value falling within a particular interval (continuous).

Characteristic Samplers

Probability distribution functions (PDFs) are optionally continuous or discrete. In the continuous case the PDF is represented by a function. In the discrete case, the variable space is binned into a series of discrete values. In both the continuous and discrete cases, PDFs are generated by first decomposing the PDF into a set of samplers that are characteristic of the PDF and then propagating those samplers via computations through the DSSM (prior generation) and sensor data integrator (posterior generation). Herein a sampler is a combination of a value and label. The value is associated with the x-axis of the PDF, which denotes state, model, or joint parameters. The label is associated with the y-axis of the PDF, which denotes the probability. Examples of labels are: weight, frequency, or any arbitrary moment of a given distribution, such as a first Gaussian moment. A powerful example of characteristic sampler use is decomposing the PDF into a series of state values with attached first Gaussian moment labels. This sum of several Gaussian distributions with different values and moments usually gives accurate approximations of the true PDF.

Dynamic State-Space Model

The dynamic state-space model 210 is further described herein.

Figure 7:
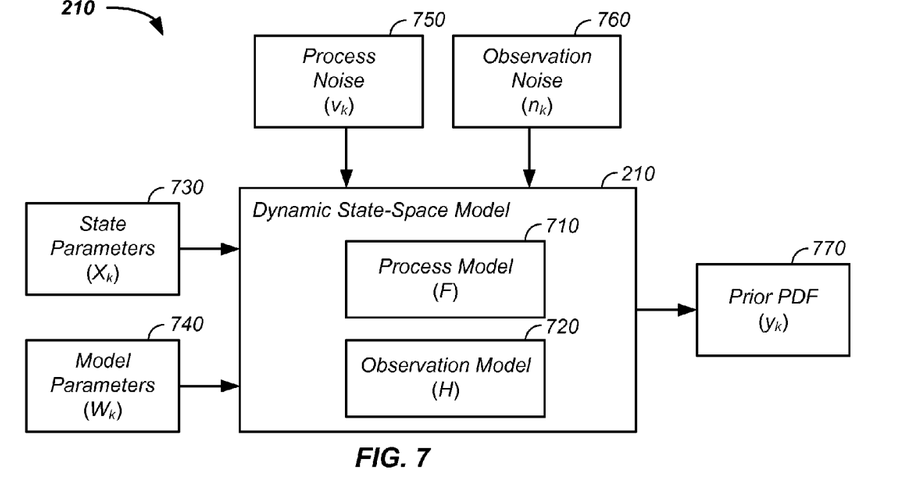
FIG. 7 provides inputs and internal operation of a dynamic state-space model.

Referring now to FIG. 7, schematics of an exemplary dynamic state-space model 210 (DSSM) used in the processing of data is provided. The dynamic state-space model 210 typically and optionally includes a process model 710 and/or an observation model 720. The process model 710, F, which mathematically represents mechanical processes involved in generating one or more mechanical parameters, is measured by sensor and/or a sensor sensing a mechanical action or motion and describes the state of the mechanical apparatus over time in terms of state parameters. This mathematical model optimally includes mathematical representations accounting for process noise 750, such as mechanically caused artifacts that may cause the sensor to produce a digital output that does not produce an accurate measurement for the mechanical parameter being sensed. The dynamic state-space model 210 also comprises an observational model 720, H, which mathematically represents processes involved in collecting sensor data measured by the mechanical sensor. This mathematical model optimally includes mathematical representations accounting for observation noise produced by the sensor apparatus that may cause the sensor to produce a digital output that does not produce an accurate measurement for a mechanical parameter being sensed. Noise terms in the mathematical models are not required to be additive.

While the process and observational mathematical models 710, 720 are optionally conceptualized as separate models, they are preferably integrated into a single mathematical model that describes processes that produce a mechanical parameter and processes involved in sensing the mechanical parameter. The process and observation integrated model, in turn, is integrated with a processing engine within an executable program stored in a data processor, which is configured to receive digital data from one or more sensors and to output data to a display and/or another output format.

Still referring to FIG. 7, inputs into the dynamic state-space model 210 include one or more of:

state parameters 730, such as the initial state parameter probability distribution function 312 or the new PDF;

model parameters 740, such as the initial noise parameter probability distribution function 314 or an updated model parameter from the unsupervised machine learning module 532;
process noise 750; and/or
observation noise 760.

Valve Bearing

Figure 8:
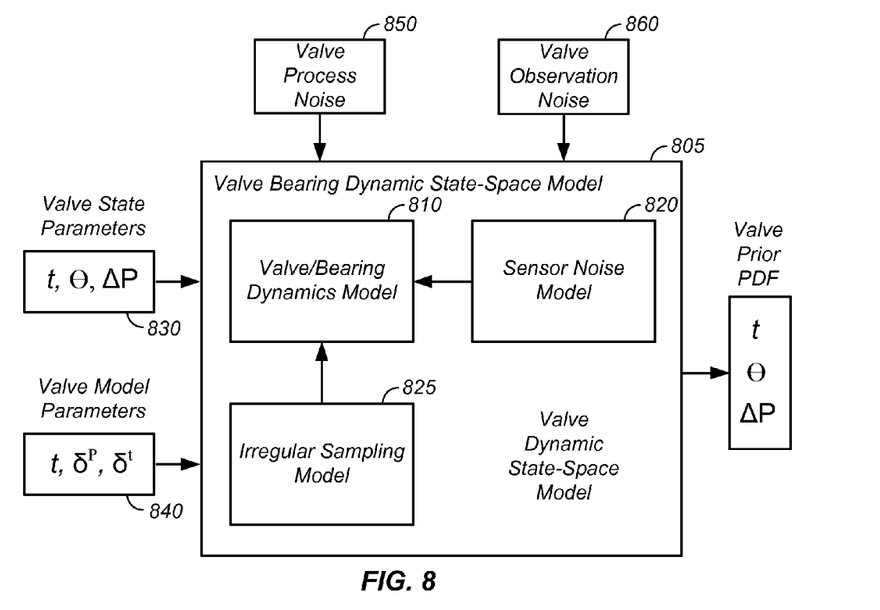
FIG. 8 illustrates inputs and internal models for a valve bearing health dynamic state-space model.

A first non-limiting specific example is used to facilitate understanding of the dynamic state-space model 210. Referring now to FIG. 8, a valve bearing dynamic state-space model 805 flow diagram is presented. Generally, the valve dynamic state-space model 805 is an example of a dynamic state-space model 210. The valve dynamic state-space model 805 is provided sensor data 122, such as a measured load on the bearing. Optionally, the load on the bearing is provided as a function of rotation of the valve, such as under the control of the controller 110. The valve dynamic state-space model 805 operates in conjunction with the probabilistic updater 220 to form an estimate of remaining valve life of the bearing without removal of the valve from its system.

Figure 9A:
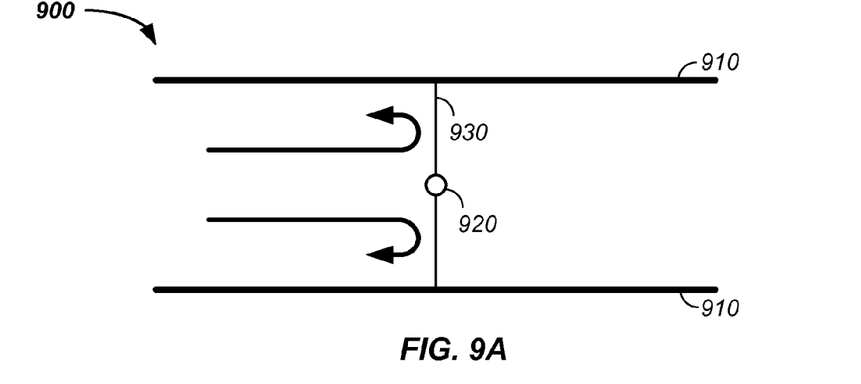
Figure 9B:
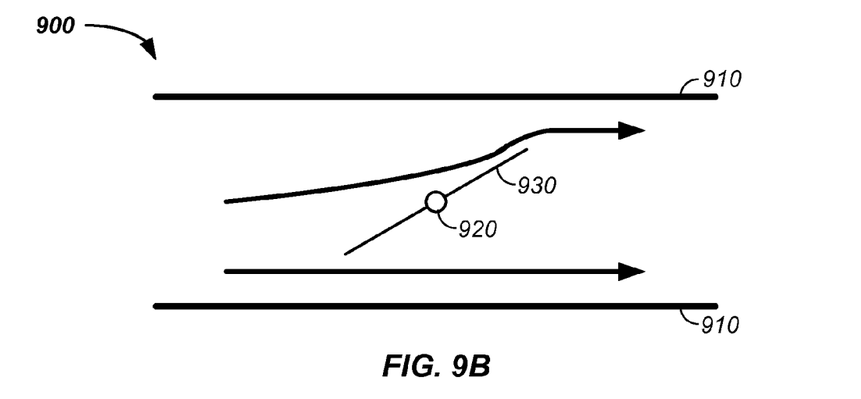
Figure 9C:
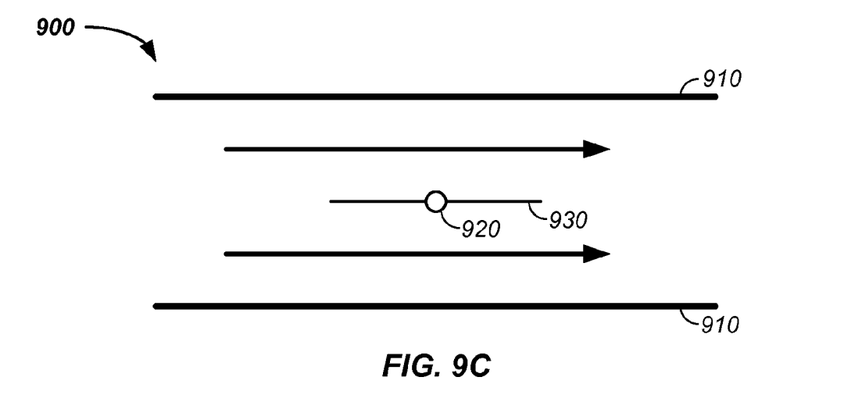

To facilitate description of the valve bearing dynamic state-space model 805, a non-limiting valve example is provided. Referring now to FIGS. 9A-C, a figuratively illustrated valve 900 is schematically represented in a closed, semi-open, and open state, respectively. Generally, a valve 900 is a pipe fitting. Herein, a valve 900 is a device that regulates the flow of a fluid, liquid, gas, fluidized solids, and/or a slurry by opening, closing, or partially obstructing various passageways. Herein, for clarity a fluid is used as a non-limiting example of a substance passing in a pipe 910 through the valve 900. In an open valve 900, fluid flows in a direction from higher pressure to lower pressure. The valve 900 optionally uses a bearing 920 in opening and shutting of the valve by movement of a valve blocking element 930.

Referring again to FIG. 8, the valve bearing dynamic state-space model 805 is further described. The valve bearing dynamic state-space model 805 includes one or more models describing the valve/bearing system. For example, a valve dynamics model 810 is used. The valve dynamics model 810 is a probabilistic model describing the bearing. A particular case is used to further describe the valve bearing dynamic state-space model 805. In this case, movement of the bearing 920 is described using a force model, such as movement of the valve blocking element through an angle or rotation, theta. Particularly, change in the rotation of the valve blocking element 930 with rotation of the valve bearing 920 is described according to equation 1, where t is time, P is pressure, and $\alpha$ is the proportionality constant, which is the bearing coefficient of friction that yields information on the state or wear of the bearing 920.

$$\frac{d\theta}{dt} = \alpha \Delta P \qquad (eq.\ 1)$$

Physics relates the angular momentum, $d^2\theta/dt^2$ to the pressure according to equation 2, $$I\frac{\partial^2 \theta}{\partial t^2} = a\Delta P - bR \qquad (eq.\ 2)$$

where movement is related to change in pressure, I is the moment of inertia of the ball bearing assembly, a is a proportionality constant, b is the bearing coefficient, and R is the effective radial load on the bearing. Hence, the valve dynamics model 810 yields information on the bearing 920 through changes in pressure. The valve dynamics model 810 optionally receives inputs from one or more additional models, such as an irregular sampling model 825 and/or a sensor noise model 820. For instance, the irregular sampling model yields information where the time interval between sampling is non-uniform or non-constant. The valve bearing dynamic state-space model 805 receives inputs, such as one or more of:
valve state parameters 830;
valve model parameters 840;
valve process noise 850; and
valve observation noise 860.

Examples of valve state parameters 830, corresponding to state parameters 730, include: time, theta, and change of pressure. Examples of valve model parameters 840, corresponding to the more generic model parameters 740, include: time, t, change in pressure since the last reading, $\delta^P$, and change in time since the last reading, $\delta^t$. In this example, the output of the valve dynamic state-space model 805 is a valve prior probability distribution function with parameters matching the input valve state parameters 830 after operation on by the valve dynamics model 810. Generally, the valve dynamic state-space model 805 is an example of a dynamic state-space model 210, which operates in conjunction with the probabilistic updater 220 to form an estimate of remaining valve life using a measured load of the bearing, which is an example of sensor data 122, for the valve 900 without removal of the valve from its system.

Pipe

Figure 10:
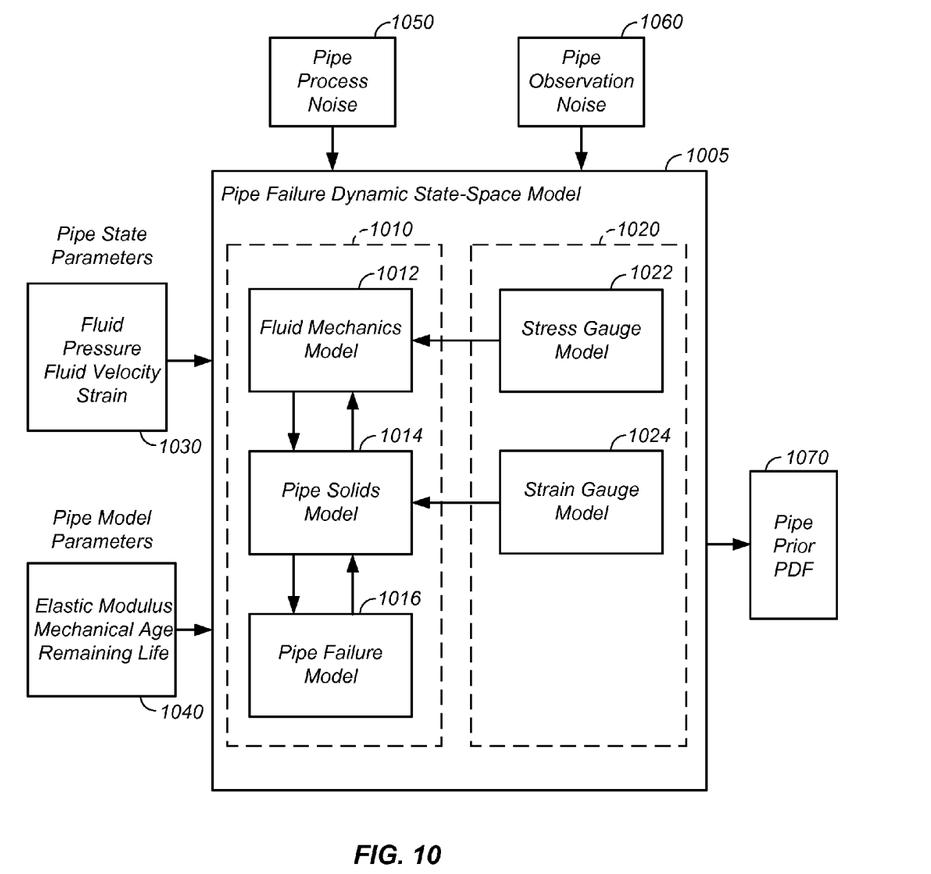
FIG. 10 provides an exemplary pipe failure dynamic state-space model.

A second non-limiting specific example is used to facilitate understanding of the dynamic state-space model 210. Referring now to FIG. 10, a pipe failure dynamic state-space model 1005 flow diagram is presented. Generally, the pipe failure dynamic state-space model 1005 is an example of a dynamic state-space model 210. The pipe failure dynamic state-space model 1005 is provided sensor data 122, such as fluid pressure, fluid velocity and/or strain. The pipe failure dynamic state-space model 1005 operates in conjunction with the probabilistic updater 220 to form an estimate of risk of pipe failure.

More particularly, piping often must be able to withstand harsh chemicals, high pressure, temperature gradients, and vibrations due to turbulent flows. All of these, even when operating within design specifications, contribute to mechanical aging. Real time monitoring and diagnostics of piping can be accomplished, for instance, by the placement of strain gauges at one or several points on the pipe inner or outer surfaces. The vibration data can be processed by the present invention in order to extract the health of the pipe component and also estimate the remaining useful life or some other measure of failure.

Referring to FIG. 10, the pipe failure dynamic state-space model 1005 is further described. The pipe failure dynamic state-space model 1005 optionally includes a pipe failure process model 1010 corresponding to the more generic process model 710 and/or a pipe failure observation model 1020 corresponding to the more generic observation model 720. The pipe failure process model 1010 optionally includes one or more models describing the pipe system. For example, a fluid mechanics model 1012 is optionally used with still additional optional inputs from a pipe solids model 1014 and/or a pipe failure model 1016. Similarly, the pipe failure observation model 1020 optionally includes one or more models, such as a stress gauge model 1022 and/or a strain gauge model 1024. The model(s) of the pipe failure observation model 1020 optionally serve as inputs to the pipe failure process model 1010.

As with the valve dynamics model 810, the pipe failure dynamic state-space model 1005 is a probabilistic model describing the pipe system with one or more inputs, such as one or more of:

pipe state parameters 1030;
pipe model parameters 1040;
pipe process noise 1050; and
pipe observation noise 1060.

Examples of pipe state parameters 1030, corresponding to the more generic state parameters 730, include: fluid pressure, fluid velocity, and/or strain. Examples of pipe model parameters 1040, corresponding to the more generic model parameters 740, include: an elastic modulus, mechanical age, and/or remaining life. In this example, the output of the pipe dynamic state-space model 1005 is optionally a pipe failure prior probability distribution function. Generally, the pipe failure dynamic state-space model 1005 is an example of a dynamic state-space model 210, which operates in conjunction with the probabilistic updater 220 to form an estimate of remaining pipe life using measured inputs that do not require disassembly of the pipe system. The system is applicable to complex piping systems with many optional valves.

Generally, in various embodiments, the probabilistic digital signal processor 200 is optionally used to filter output from any mechanical device using appropriate physical models, which optionally include chemical, electrical, optical, mechanical, or fluid based models.

Several examples are provided to further clarify the intelligent data extraction system 100.

In one example, an apparatus for estimation of state of mechanical health of a mechanical element, includes a probabilistic data signal processor embedded in a computer, where the probabilistic data signal processor includes: a dynamic state-space model comprising at least one of: (1) a process model and (2) an observation model; a probabilistic updater configured to generate a posterior probability distribution function using both: (1) a prior probability distribution function output from the dynamic state-space model and (2) readings from a sensor, the sensor configured to provide time dependent readings related to a mechanical state of the mechanical element; and a probabilistic sample module configured to operate on the posterior probability distribution function to generate an output in the form of probabilities of state of health of the mechanical element.

In another example, a method for estimating state of mechanical health of a mechanical element includes the steps of: collecting with a sensor time dependent readings related to a mechanical state of the mechanical element; calculating a prior probability distribution function with a probabilistic data signal processor, where the probabilistic data signal processor includes a dynamic state-space model comprising at least one of: a process model; and an observation model; determining a posterior probability distribution function through combination of: (1) the prior probability distribution function output from the dynamic state-space model and (2) the readings from the sensor; and using the posterior probability distribution function, generating an output comprising an estimate of state of health of the mechanical element.

In yet another example, a method for estimation of state of health of a system includes the steps of: providing a probabilistic data signal processor operational in a computer, where the probabilistic data signal processor includes: a probabilistic updater and a dynamic state-space model; using the probabilistic processor to: (1) operate on a sensor provided deterministic state reading of the system and (2) convert the deterministic state reading into a probability distribution function, where the dynamic state-space model includes a probabilistic model configured to operate on the probability distribution function, where the probabilistic data signal processor iteratively circulates the probability distribution function in the dynamic state-space model and the probabilistic updater, where the probabilistic data signal processor estimates probability of truth of the state reading, and where the probabilistic data signal processor is configured to provide an output probability distribution function representative of state of health of the system.

Diagnosis Prognosis

Figure 11:
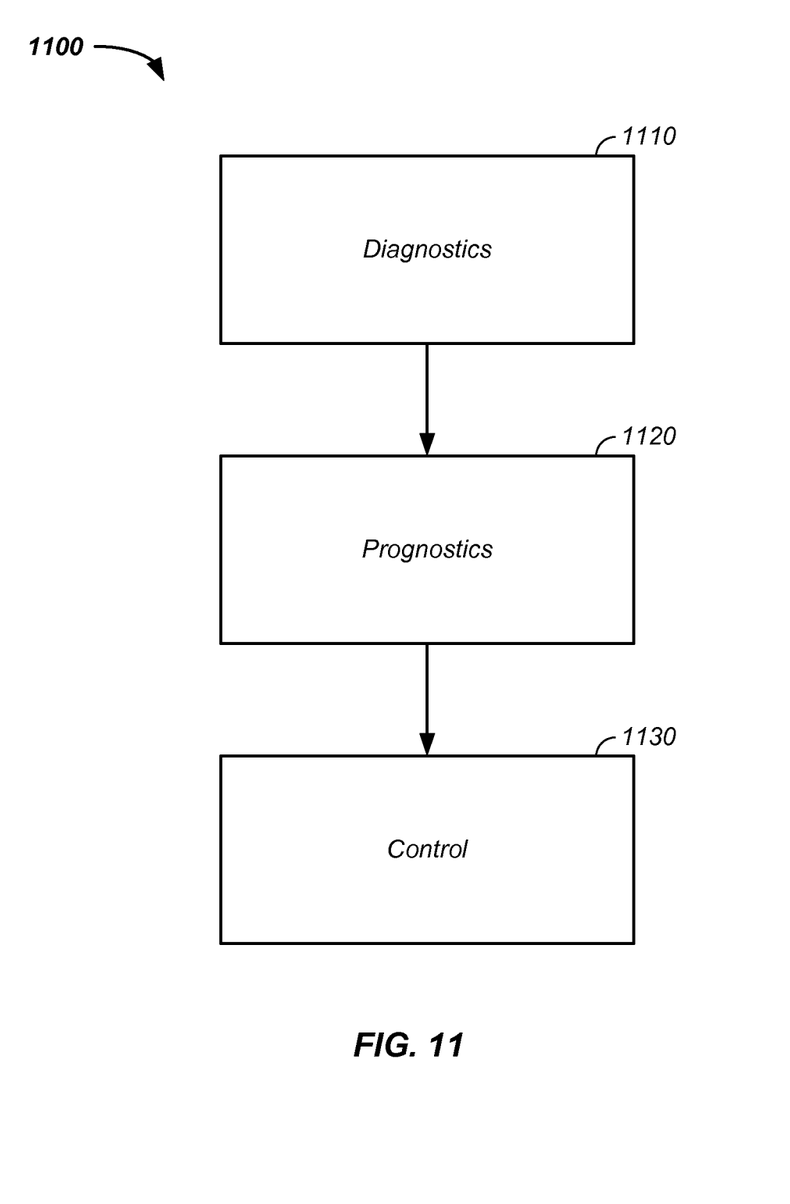
FIG. 11 provides a flowchart of dynamic state-space model diagnostics used as prognosis and control.

Referring now to FIG. 11, the output of the probabilistic digital signal processor 200 optionally is used to diagnose 1110 a system element or component. The diagnosis 1110 is optionally used in a process of prognosis 1120 and/or in control 1130 of the system.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. An apparatus for estimation of state of mechanical health of a mechanical element, comprising:
   a probabilistic data signal processor embedded in a computer, said probabilistic data signal processor comprising:
      a dynamic state-space model comprising:
         a process model; and
         an observation model;
      a probabilistic updater configured to generate a posterior probability distribution function using both: (1) a prior probability distribution function output from said dynamic state-space model and (2) readings from a load sensor, wherein the mechanical element comprises a valve bearing of a valve, said valve comprising a pipe fitting configured to regulate flow of a substance through a pipe, said load sensor configured to provide time dependent measurements related to load on the valve bearing of the valve; and
      a probabilistic sample module configured to operate on said posterior probability distribution function to generate an output in the form of at least one probability of state of health of said valve.

2. The apparatus of claim 1, further comprising:
   an iterative control module configured to:
      control said load sensor; and
      control physical rotational movement of said valve bearing using said posterior probability distribution function in an iterative control loop, said time dependent readings of said load sensor correlated with said movement of said valve bearing.

3. The apparatus of claim 1, wherein said time dependent readings comprise data related to load on said valve bearing, wherein output correlated with the posterior probability distribution function relates to an estimated remaining life of said valve.

4. The apparatus of claim 1, wherein the time dependent readings from said load sensor comprise deterministic readings, said probabilistic data signal processor configured to convert said deterministic readings into said output, said output comprising a probability distribution function representative of state of health of said valve.

5. The apparatus of claim 1, wherein said process model of said dynamic state-space model comprises a valve dynamics model, said valve dynamics model configured to operate on at least pressure readings from said load sensor.

6. The apparatus of claim 5, wherein said observation model of said dynamic state-space model comprises a load sensor noise model configured to use mathematical representations accounting for observation noise produced by said load sensor.

7. The apparatus of claim 5, further comprising:
an irregular sampling model configured to provide non-uniform sampling information to said valve dynamics model.

8. The apparatus of claim 1, wherein said process model of said dynamic state-space model comprises a pipe failure dynamic state-space model configured to operate on at least one of:
fluid velocity data;
stress data from a stress gauge; and
strain data from a strain gauge.

9. The apparatus of claim 8, wherein said output comprises a probability function estimating likelihood of pipe failure.

10. A method for estimating state of mechanical health of a mechanical element, comprising the steps of:
collecting with a sensor time dependent readings related to a mechanical state of the mechanical element, wherein the mechanical element comprises a valve bearing of a valve, said valve comprising a pipe fitting configured to regulate flow of a substance through a pipe, said sensor configured to measure load on said valve bearing;
calculating a prior probability distribution function with a probabilistic data signal processor, said probabilistic data signal processor comprising:
a dynamic state-space model comprising:
a process model; and
an observation model using the readings from said sensor,
determining a posterior probability distribution function through combination of: (1) said prior probability distribution function output from said dynamic state-space model and (2) the readings from said sensor; and
using said posterior probability distribution function, generating an output comprising an estimate of state of health of the mechanical element.

11. The method of claim 10, wherein said estimate comprises a state of health probability function of the valve bearing.

12. The method of claim 10, wherein said sensor yields a first state parameter reading, wherein said output comprises an output to a second state parameter, wherein said first state parameter is different from said second state parameter.

13. The method of claim 12, wherein said first state parameter comprises a pressure reading, wherein said second state parameter comprises a measure related to a coefficient of friction of rotation of said valve bearing.

14. The method of claim 10, further comprising the step of:
operating on said posterior distribution function with a probabilistic sampler to generate an updated parameter, said updated parameter iteratively passed to said dynamic state-space model.

15. The method of claim 14, further comprising the step of:
resampling output of said probabilistic sampler to form a new probability distribution function.

16. The method of claim 15, said step of resampling using a sigma point Kalman filter.

* * * * *